United States Patent
Ljungquist

Patent Number: 5,817,055
Date of Patent: Oct. 6, 1998

[54] DUAL-CHAMBER INJECTION CARTRIDGE

[75] Inventor: Olle Ljungquist, Täby, Sweden

[73] Assignee: Pharmacia & Upjohn Aktiebolag, Stockholm, Sweden

[21] Appl. No.: 477,607

[22] Filed: Jun. 7, 1995

Related U.S. Application Data

[63] Continuation-in-part of Ser. No. 196,194, Feb. 24, 1994, Pat. No. 5,472,422.

[30] Foreign Application Priority Data

Jul. 7, 1992 [SE] Sweden .................................. 9202108

[51] Int. Cl.$^6$ ............................................. A61M 37/00
[52] U.S. Cl. .............................. 604/89; 604/82; 604/232
[58] Field of Search ........................ 604/89, 82, 83, 604/90, 84, 56, 57, 91, 92, 232, 234, 236, 238

[56] References Cited

U.S. PATENT DOCUMENTS

| | | |
|---|---|---|
| 2,591,046 | 4/1952 | Brown . |
| 2,591,706 | 4/1952 | Lockhart . |
| 2,665,690 | 1/1954 | Lockhart . |
| 3,436,109 | 4/1969 | Loose ............................................. 65/36 |
| 3,494,359 | 2/1970 | Zackheim . |
| 4,078,910 | 3/1978 | Dalgoutte ..................................... 65/36 |
| 4,116,655 | 9/1978 | Lewis ........................................ 65/4.21 |
| 4,183,737 | 1/1980 | Chown ...................................... 65/4.21 |
| 4,414,471 | 11/1983 | Rines ........................................... 385/27 |
| 4,417,913 | 11/1983 | Davis ........................................ 65/59.1 |
| 4,439,184 | 3/1984 | Wheeler . |
| 4,469,482 | 9/1984 | Lissenburg et al. . |
| 4,613,326 | 9/1986 | Szwarc . |
| 5,143,531 | 9/1992 | Kramer ..................................... 65/59.34 |
| 5,167,686 | 12/1992 | Wong ........................................... 65/36 |
| 5,177,806 | 1/1993 | Abbott ........................................ 385/76 |

FOREIGN PATENT DOCUMENTS

| | | |
|---|---|---|
| 0 172 990 | 3/1986 | European Pat. Off. . |
| 0 207 544 | 1/1987 | European Pat. Off. . |
| 0012496 | 1/1979 | Japan ........................................... 65/36 |
| 0109014 | 6/1989 | Japan ......................................... 65/4.1 |
| 80841 | 10/1952 | Norway . |
| 1044610 | 9/1983 | U.S.S.R. ................................... 65/59.1 |

OTHER PUBLICATIONS

Technical Data Sheet, Carpenter Technology, Carpenter Steel Division, "Carpenter Free–Cut Invar '36'", (6–70) 2 pages.

"408 Glass" Product Information Sheet, GBC Materials Corporation of Letrobe, Pennsylvania, 1 page.

Primary Examiner—Michael Powell Buiz
Assistant Examiner—N. Kent Gring
Attorney, Agent, or Firm—Pollock, Vande Sande & Priddy

[57] ABSTRACT

An injection cartridge of the dual-chamber type, which comprises a cylindrical cartridge barrel having a front chamber for a solid product and a rear chamber for a liquid product. The chambers are sealingly separated by a displaceable piston of a resilient material, and have an openable bypass connection for liquid from the rear chamber to the front chamber and a resilient sealing closure of the front end of the front chamber.

10 Claims, 2 Drawing Sheets

5,817,055

DUAL-CHAMBER INJECTION CARTRIDGE

This application is a Continuation-In-Part of U.S. application Ser. No. 08/196,194, filed Feb. 24, 1994 now U.S. Pat. No. 5,472,422; and PCT application PCT/SE94/00864 Filed Sep. 16, 1994, the entire disclosures of both of which are hereby incorporated by reference.

FIELD OF THE INVENTION

The present invention refers to injection cartridges of the dual-chamber type. More specifically, it refers to improvements in injection cartridges of the dual-chamber type, whereby sterility of the components in the cartridge may be assured.

BACKGROUND OF THE INVENTION

Injection cartridges of the dual-chamber type have found a very wide use in the administering of injectable preparations which are not stable as a solution or dispersion in a liquid phase. As examples of such preparations may be mentioned certain protein compounds and hormones, such as growth hormones. These preparations are provided in a dry form, which is mixed with a liquid phase, usually water or an aqueous solution, immediately before the administering.

An injection cartridge of the dual-chamber type is generally shaped as a tubular barrel, which is divided into a front chamber and a rear chamber by means of a front piston. The front chamber contains the dry component of the injectable preparation, and is closed at its front end by a closure that permits the establishment of a liquid connection with the outside. Such a closure may be in the form of a rubber septum that may be pierced by a hollow needle for withdrawing or expelling a liquid mixture from the front chamber. The rear chamber is filled with the liquid component of the injectable preparation, usually water or an aqueous solution, and is closed at its rear end by a rear piston.

When the injectable preparation is to be prepared, pressure is applied on the rear piston to move it forward. This pressure is transmitted through the essentially incompressible liquid to the front piston, such that this piston is also moved forward. By this forward movement, the front piston activates a bypass connection, such that the liquid in the rear chamber can flow over into the front chamber by the action of the forward movement of the rear piston, to be mixed with the solid component of the injectable preparation. When all of the liquid in the rear chamber has been made to flow over into the front chamber, the front face of the rear piston will abut the rear face of the front piston. On further forward movement of the rear piston, the two pistons will act as one single piston to expel the mixed injectable preparation from the front chamber through the liquid connection mentioned above. Alternatively, the front chamber may serve as a reservoir for the mixed injectable preparation, and portions thereof may be withdrawn through the liquid connection.

The bypass connection for the liquid from the rear chamber to the front chamber may be arranged as a channel in the interior wall of the barrel of the cartridge. This channel is exposed by the front piston on its movement forward, to afford a liquid connection between the two chambers. Other arrangements are also possible.

When the injectable preparation is prepared from the two components, the injection cartridge is usually placed in a holder device provided with means for applying the pressure on the rear piston. The holder device may also be provided with means for metering and administering doses of the mixed injectable preparation.

The design and function of injection cartridges of the dual-chamber type is well-known to those skilled in the art, and need not be described here in more detail. Also, a number of the above-mentioned holder devices are well-known, and some of them are commercially available.

In the manufacture of injection cartridges of the dual-chamber type, it is, of course, of the utmost importance that sterility is maintained, so that no risk of microbial contamination of the injectable preparation will arise. However, this has been a problem with the prior art injection cartridges of the dual-chamber type.

In the prior art process for manufacture, the empty cartridges are provided with the front piston in place. The barrel of the cartridge is shaped as a cylindrical tube, which may be shaped as a bottleneck at its front end to receive the closure, and which usually consists of a rubber septum and a metal capsule having an opening in its middle. The front chamber is filled with a solution of the solid component of the injectable preparation, and the cartridge with its contents is then subjected to a freeze-drying process to evaporate the solvent and afford the component in a dry solid form. The front end of the cartridge is then closed with the closure means, and the rear chamber of the cartridge is filled with the liquid component of the injectable preparation and is closed by insertion of the rear piston.

All these operations must be carried out under aseptic or sterile conditions to assure against contamination by microorganisms. The finished cartridge cannot be heat sterilized by autoclaving, as this would degrade the sensitive solid component of the injectable preparation. The most critical of these operations is the filling of the cartridge containing the solid component with the liquid component, and the sealing of the rear chamber with the rear piston. In this operation, there is a considerable risk of microbial contamination.

It would be preferable to be able to fill the cartridge with the liquid component in the rear chamber and seal this chamber as a first step and then sterilize this assembly by autoclaving, and subsequently fill the front chamber with the solution of the solid component and carry out the freeze-drying step. However, this has not been possible, due to the fact that the cartridge with the liquid component in the rear chamber cannot be subjected to the vacuum applied during the freeze-drying step. The pressure prevailing in the rear chamber with the liquid will strive to expel the front and rear pistons from the barrel of the cartridge, and even if it is possible to secure the rear piston by some suitable holder arrangement during the freeze-drying step, this has not been possible for the front piston. Thus, during the freeze-drying step, the front piston will move forward by the influence of the pressure in the rear chamber, and will push out the solution of the solid component from the front chamber.

SUMMARY OF THE INVENTION

By the present invention, the above described disadvantages are eliminated. An injection cartridge of the dual-chamber type is provided, which may be subjected to a freeze-drying process while its rear chamber is filled with a liquid, without any risk of its pistons being displaced by the influence of a pressure difference between the front and the rear chamber. The pressure difference is usually about one 1.1 bars, which corresponds to the case when the contents of the front chamber are freeze-dried under vacuum conditions, while the rear chamber is filled with a liquid at atmospheric pressure. In such a case, there is consequently a vacuum in front of the piston and essentially atmospheric pressure behind the piston. Small deviations in this pressure differential are possible, mostly dependent on the temperature of the liquid in the rear chamber and on the ambient pressure of the atmosphere.

Thus, the present invention refers to an injection cartridge of the dual-chamber type, which comprises a cylindrical cartridge barrel having a front chamber for a solid product and a rear chamber for a liquid product. The chambers are sealingly separated by a displaceable piston of a resilient material, and have an openable bypass connection for liquid from the rear chamber to the front chamber and a resilient sealing closure of the front end of the front chamber. What characterizes the invention is that in the cartridge barrel is arranged a constriction such that the cartridge barrel has a non-circular cross-section at the constriction. The invention is also characterized in that before the liquid bypass connection has been opened, the separating piston is situated in the vicinity of the rear of the constriction. According to such an arrangement, the constriction exerts a resistance against a forward displacement of the piston, such that the piston is prevented from moving forward when there is a vacuum in front of the piston and essentially atmospheric pressure behind the piston. Furthermore, the piston, during a displacement forward through the constriction while overcoming the resistance is deformed such that said liquid bypass connection is established.

The invention further refers to a method for manufacturing an injectable preparation of a pharmaceutically active agent suitable for storage in a dual-chamber injection cartridge according to the invention. The method includes the step of A. filling the rear chamber of said injection cartridge with the liquid component of the preparation. The rear chamber and is sealed and the injection cartridge is optionally subjected to a heat sterilization. The solution of the pharmaceutically active agent is charged in the front chamber of the injection cartridge. Then the injection cartridge is subjected to a freeze-drying process. The front chamber of the injection cartridge is sealed.

In the preferred embodiment of the invention, the front and rear chambers are separated by a displaceable piston that is prevented from being displaced during the freeze-drying step. By the application of additional force, however, the piston may be deformed sufficiently to pass through the constriction. By becoming deformed, the piston will allow the liquid to pass by and enter the front chamber to be mixed with the solid, pharmaceutically active component. Through the injection cartridge and the method of the present invention, it has for the first time become possible to freeze-dry the solution of the active agent in the front chamber of the cartridge while the liquid component of the injectable preparation is already present in the rear chamber. This brings about considerable advantages, as has been described in the foregoing.

Preferably, the constriction has such a shape that the cartridge barrel has an oval or a dumbbell-shaped cross-section at the site of the constriction. It is also possible that the constriction has an unsymmetrical shape. Thus, the cartridge barrel may be compressed from essentially one side, such that, for example, a constriction is formed having a narrowing cross-section from the rear end of the barrel to the front end of the barrel.

DETAILED DESCRIPTION OF THE DRAWING

Figure 1:
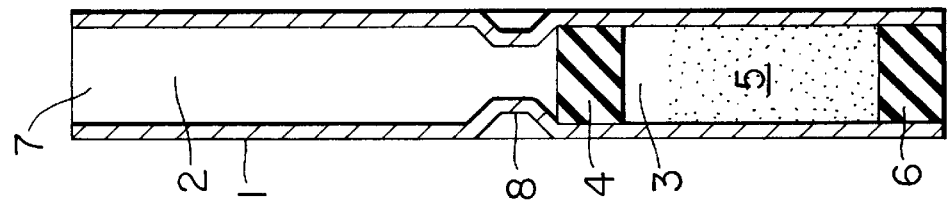
FIG. 1 shows a sectional view of an injection cartridge of the invention with a liquid filled into its rear chamber.

FIG. 1 is a schematic longitudinal sectional view of an injection cartridge according to the invention. The cartridge comprises a barrel 1, which is divided into a front chamber 2 and a rear chamber 3 by means of a displaceable front piston 4. The rear chamber 3 contains a liquid 5 and is sealed at its rear end by a displaceable rear piston 6. The liquid is primarily sterile water or a sterile aqueous solution. However, other types of liquids, such as emulsions or suspensions are also possible. At its front end 7, the cartridge barrel 1 is shaped to receive a closure of a known type, such as a rubber septum and a metal capsule. Preferable, the closure is resilient, and may further be pierceable. As such a closure is well-known to those skilled in the art, it is not shown in the drawing.

According to the invention, the barrel 1 of the cartridge is provided with a constriction 8. The front piston 4 is situated in the vicinity of the constriction 8. In preferred embodiments, the front piston 4 is situated close to or preferably immediate to the rear of said constriction 8. Thus, the constriction 8 prevents any inadvertent displacement forward of the front piston 4.

The barrel 1 of the cartridge is usually made from glass or a plastic material. The constriction may be arranged by pinching the barrel with a suitable pinching tool while the barrel material has been softened by heating. The constriction may also be arranged by securing a ring-shaped constricting piece inside the barrel at a suitable position, if softening by heat is not suitable. It is also possible that the constriction has an unsymmetrical shape. Thus, the cartridge barrel may be compressed from essentially one side, such that, for example, a constriction is formed having a narrowing cross-section from the rear end of the barrel to the front end of the barrel.

Figure 2:
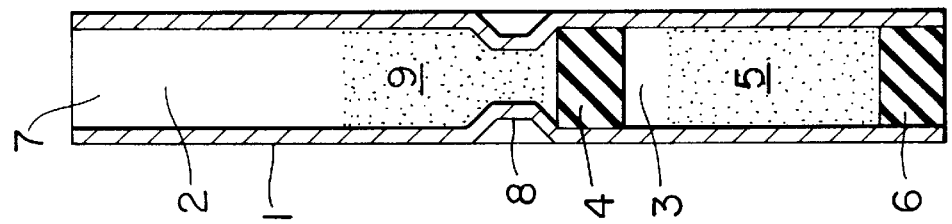
FIG. 2 shows the same cartridge with a solution of the solid component filled into the front chamber.

FIG. 2 is a schematic sectional view of the same injection cartridge, where the front chamber 2 has been filled with a solution 9 of the solid component of the injectable preparation. Prior to the filling of the solution in the front chamber, the cartridge with the liquid component enclosed in the rear chamber 3 has been subjected to a heat sterilizing process to render it sterile before the solution 9 is filled into the front chamber 2. Such a sterilizing process is possible in a pressure autoclave, where the pressure counteracts the tendency of the liquid 5 in the rear chamber 3 to expand under the influence of the heat and displace one or both of the front piston 4 and the rear piston 6.

Figure 3:
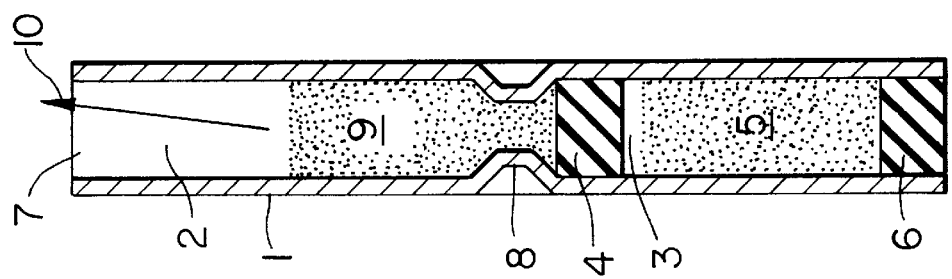
FIG. 3 shows the same cartridge during the freeze-drying process.

FIG. 3 shows a schematic longitudinal sectional view of the same injection cartridge while it is subjected to a freeze-drying process. The liquids 5 in the rear chamber and 9 in the front chamber are here frozen, and vapor escapes from the frozen solution 9, as is shown by the arrow 10.

As the freeze-drying is carried out under vacuum, the pressure prevailing in the rear chamber 3 strives to displace the front piston 4 forward and the rear piston 6 rearward. However, the constriction 8 prevents the displacement forward of the front piston 4, while the rear piston 6 is held secure by a clamping device of a known type (not shown). Thus, nothing of the contents of the rear chamber 3 escape from the chamber.

Figure 4:
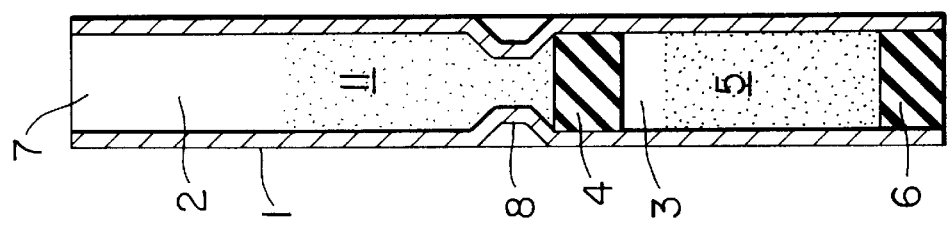
FIG. 4 after completion of the freeze-drying process.

FIG. 4 shows a schematic sectional view of the same cartridge after the freeze-drying process has been completed. The solution in the front chamber 2 has been evaporated to give a solid residue 11, which is the solid component of the injectable preparation. The frozen liquid 5 in the rear chamber has thawed into its liquid state. Also, the front chamber has been sealed by a suitable closure (not shown) at its front end 7. This is usually carried out inside the freeze-drying chamber after completion of the freeze-drying process, by the use of suitable equipment, which is known to those skilled in the art.

After the vacuum in the freeze-drying chamber has been released, the cartridge may be taken out. It is suitable to release the vacuum by introducing an inert gas, suitably nitrogen gas, to maintain the quality of the product. The contents of the two chambers 2 and 3 is now completely sterile, and the cartridge may be stored until it is to be used for administering one or more injections, or for the preparation of an injectable preparation to be withdrawn from the cartridge.

Figure 5:
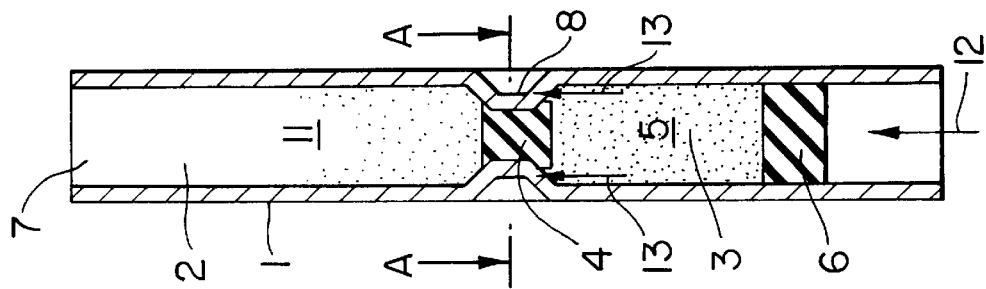
FIG. 5 shows the same cartridge during the displacement forward of the front piston and the opening of the liquid bypass connection.

FIG. 5 shows a schematic longitudinal sectional view of the injection cartridge of the invention when the liquid in the rear chamber is to be mixed with the solid component in the front chamber. A forward pressure is applied on the rear piston 6, as is symbolized by the arrow 12. This pressure will be transmitted through the essentially incompressible liquid 5 to act on the front piston 4. At a sufficiently high pressure on the rear piston 6, the front piston 4 will overcome the resistance of the constriction 8 in the barrel 1 and will be urged into the said constriction. This will be possible because the front piston 4 is manufactured from a suitably resilient material, such as rubber. When the front piston 4 is urged into the constriction 8, it will be deformed, and will strive to adapt to the cross-section of the constriction 8. However, as the cross-section is non-circular, the resilience of the piston material is not sufficient to allow the piston 4 to adapt completely to the cross-section. Instead, leaks will occur between the deformed piston 4 and the interior wall of the barrel 1, to afford a bypass liquid connection from the rear chamber 3 to the front chamber 2. Thus, the liquid 5 will flow from the rear chamber 3 into the front chamber 2 under the influence of the pressure 12 acting on the rear piston 6, bypassing the deformed front piston 4, as is shown by the arrows 13. The liquid component 5 will now be mixed with the solid component 11 to dissolve it or disperse it into the injectable preparation.

When the rear piston 6 has been moved forward so far that it abuts the front piston 4, all of the liquid component 5 has been transferred to the front chamber 2. Further pressure on the rear piston 6 will make the two pistons 6 and 4 act like one single piston and will urge them through the constriction 8 out into the front chamber 2. This is possible because of the resilience of the material of the pistons 4 and 6, and after the two pistons have passed through the constriction 8, they will revert to their undeformed state and will seal against the interior wall of the barrel 1. They will then act like one single piston in the front chamber 2 for expelling the mixed injectable preparation through a liquid connection that has been opened through the closure of the front end 7. This liquid connection can consist of a hollow needle, which may be pointed at both ends for directly administering the preparation to a patient. Alternatively, the needle may be connected to a tube, which, at its other end, is connected to a needle or cannula for injection or infusion to a patient. Such arrangements are well-known to those skilled in the art, and are therefore not shown in the drawing.

Figure 7:
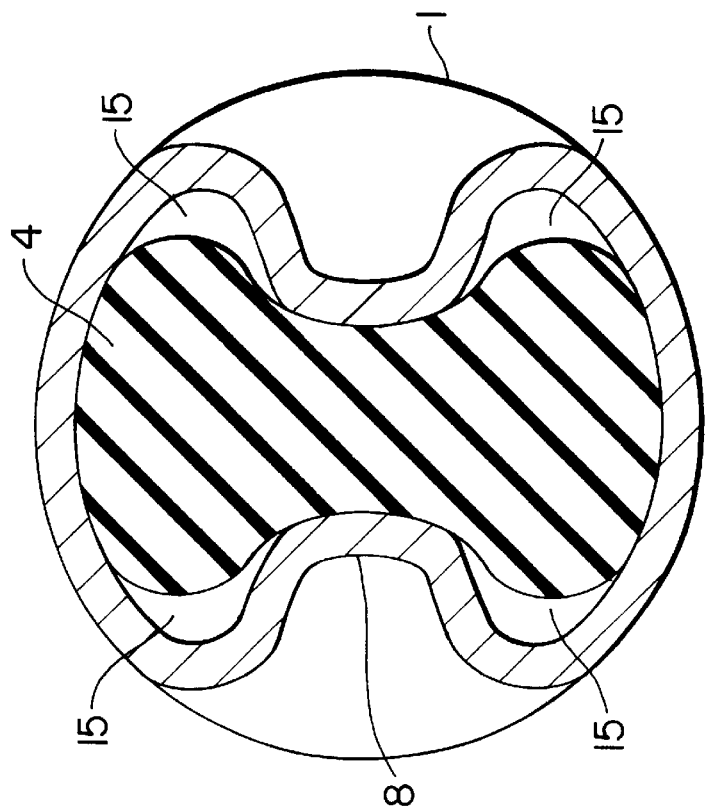
FIGS. 6 and 7 show two different shapes of the constriction in cross-sectional views. In the drawings, like parts have the same reference numbers.
Figure 6:
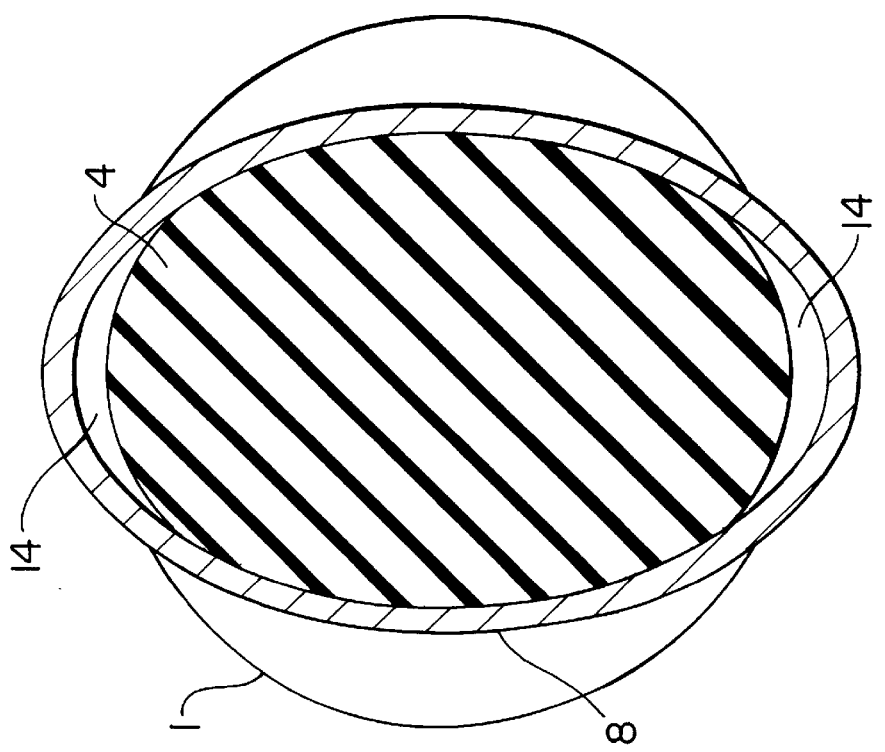

FIGS. 6 and 7 show two embodiments of the constriction 8 in the barrel 1 of the injection cartridge of the invention. The figures are cross-sectional views along the line A—A in FIG. 5.

In FIG. 6, it will be seen that the constriction 8 of the barrel 1 of the injection cartridge has an oval cross-section. The front piston 4 is deformed to adapt to this cross-section, but its resilience is not sufficient to adapt completely, and spaces 14 will form between the piston 4 and the interior wall of the barrel 1. These spaces 14 will serve as bypass connections to afford a passage of liquid from the rear chamber 3 into the front chamber 2.

FIG. 7 shows an embodiment where the constriction 8 has a cross-section that is essentially shaped like a dumbbell. When the front piston 4 is deformed and strives to adapt to this shape, spaces 15 are formed that allow the passage of liquid from the rear chamber 3 into the front chamber 2. It is also possible that the constriction has an unsymmetrical shape. Thus, the cartridge barrel may be compressed from essentially one side, such that, for example, a constriction is formed having a narrowing cross-section from the rear end of the barrel to the front end of the barrel.

Other shapes of the cross-section of the constriction 8 are also possible. What is important is that the cross-section should not be circular. A piston that is deformed to adapt to a circular cross-section having a smaller diameter will still seal against the interior wall, and will not give any spaces for a bypass flow of liquid.

The shape and size of the constriction 9 and the shape and resilience of the pistons 4 and 6 should be selected such that the front piston in its initial position in the vicinity of the rear of the constriction cannot overcome the resistance of the constriction by the action of only the pressure differential during the freeze-drying step. When additional force is applied on the piston, however, it should be able to pass through the constriction while being deformed, and be able to revert to its original shape and resilience after having passed through the constriction. These parameters may be determined by one skilled in the art by routine experiments, once the basic inventive idea has been understood.

Thus, the constriction 9 and the front piston 4 should be constructed in such a way that the force necessary to push the piston 4 into the bypass zone formed by the constriction 9 ($F_{open}$) is greater than the force arising from the pressure difference between the two faces of the piston 4 during the freeze-drying process ($F_{1yo}$). This pressure difference reaches a maximum value ($\Delta P$) of about 1.1 bars, which usually occurs in the secondary stage of the freeze-drying process, provided that the rear chamber is closed at the same pressure and temperature as is used in the secondary drying. The necessary force can then be calculated with knowledge of the interior diameter ($D_i$) of the cartridge barrel:

$$F_{open} > F_{1yo} = \Delta P_{max} \times D_i^2 \times \pi / 4$$

However, the value of $F_{open}$ should not be too high, as this will make the handling of the injection device inconvenient when the components are to be mixed. In practice, this sets a useful interval for the value of $F_{open}$. An example: If the interior diameter of the barrel is 1.5 cm, the value of $F_{1yo}$ will be about 17.7N. If the maximum necessary force for convenient handling of the device is set to about 25N, the constriction should provide an intermediate $F_{open}$ value of, say, about 20N. The selection of a suitable size of the constriction in connection with suitable dimensions and materials of the front and rear pistons 4 and 6 is well within the competence of a person skilled in this art.

For the readying of the cartridge by mixing the two components into the injectable preparation and the subsequent administering of one or more doses of the preparation, the injection cartridge is usually placed in a holder device. Such holder devices of various designs are known to those skilled in the art, and need not be described here in greater detail. They usually comprise a piston rod for moving the rear wall forward to establish the liquid bypass connection, and a metering device for the subsequent metering out of doses of the injectable preparation for administering to the patient. A number of such devices are intended to be used by a patient for administering injections to himself. Many such devices are of a disposable type, such that an emptied cartridge cannot be taken out from the device without breaking the device, thus making it impossible to use the device more than once. This is an important safety feature.

In NO-A-80 841 is disclosed a tubular ampoule a comprising two chambers that are separated by a stopper positioned in a liquid component and that is closed at one end by a movable wall. The separating stopper provides a complete seal between the two chambers while it is positioned in the constriction, and it may be pushed out into the chamber containing the solid component by applying pressure on the movable wall closing the other end of the ampoule. Once pushed out into the chamber, the stopper lies loose in the chamber and cannot serve as a piston for expelling the mixed preparation from the ampoule, as it does not seal against the interior wall of the barrel. The movable wall at the other end of the ampoule is only displaced a short distance sufficient to push out the stopper from the constriction, so that a connection is established between the two chambers, and there is no question of establishing a temporary bypass connection for a liquid. Also, the opposite end of the ampoule from the movable wall is closed permanently, and there is no arrangement of a pierceable closure at this end. Therefore, the disclosure of NO-A-80 841 will not lead a person skilled in the art to the present invention.

The injection cartridge of the present invention is manufactured from previously known materials, such as glass or plastics, and in a conventional way. As stated above, the dimensions of the constriction and the material and dimensions of the pistons are selected such that a suitable resistance is achieved against the forward movement of the pistons through the constriction. It must be ensured that the front piston is not inadvertently displaced during the freeze-drying process or the heat sterilizing process, but that it may be displaced against the resistance of the constriction by the application of a reasonably greater force, at the same time as it is temporarily deformed to afford the bypass liquid connection. The injection cartridge of the present invention may be used for any injectable preparation that is unstable in its ready-mixed state and that must be prepared immediately before use by mixing a solid and a liquid component. Examples are therapeutic proteins and peptides. Typical examples are growth hormones, certain peptides, anticancer drugs, vaccines, interleukines, monoclonal antibodies, tissue plasmin activator (tPA), erythropoietin (EPO), urokinase, streptokinase, low-molecular weight heparins and human proteins. More particularly, the human proteins are factor VIII, factor IX or antithorombin III, produced by recombinant DNA technology. Suitable liquid injectable preparations includes solutions containing human proteins, such as factor VIII, factor IX an antithrombin III, with at least one stabilizing agent, such as a surfactant. Suitable solid components of an injectable preparation include lyophilized human proteins, preferably factor VIII produced by recombinant DNA technology.

Through the present invention, it has been made possible to provide an injection cartridge of the dual-chamber type, which can be subjected to a heat-sterilizing process and a freeze-drying process while the liquid component is present in the rear chamber of the cartridge, without any risk of inadvertent displacement of the front piston separating the front chamber and the rear chamber. This will considerably decrease the risk of contamination by micro-organisms during the manufacture and preparation of the cartridges. Also, the injection cartridges of the invention do not require any important modification of the freeze-drying equipment conventionally used. This makes the invention advantageous from an economical point of view.

Furthermore, through the bypass arrangement of the invention, there will be no need for a bypass channel arranged in the wall of the cartridge, so that there will be no external projection from the barrel of the cartridge. This makes the cartridge take up less space in a holder device, which may therefore be made slimmer and less bulky, so that it will be easier for a patient to carry around.

Although the present invention has been referred to herein as a dual-chamber injection cartridge and as such includes at least two chambers and a fluid connection therebetween, it will be understood that the injection cartridge may include at least two chambers. In fact the injection cartridge may include three or more chambers. The chambers may have a variety of functions including those described above. Additionally, at least one of the chambers may contain a rinsing liquid. Furthermore, medicants or other components of an injectable preparation in addition to those described above may be included in other chambers.

In the foregoing specification, the invention has primarily been described with reference to the embodiments shown in the drawings. However, a person skilled in the art will realize that other embodiments and modifications are possible within the scope of the annexed claims.

I claim:

1. An injection cartridge of the dual-chamber type, comprising a cylindrical cartridge barrel having a front chamber for a solid component and a rear chamber for a liquid component of an injectable preparation, said chambers being sealingly separated from each other by a displaceable front piston of a resilient material, an openable bypass connection for liquid from the rear chamber to the front chamber, and a pierceable closure sealing the front end of the front chamber, characterized in that in the barrel of the cartridge is arranged a constriction such that said cartridge barrel has a non-circular cross-section at said constriction, that before said liquid bypass connection has been opened, said separating front piston is positioned close to the rear of said constriction, such that said constriction exerts a resistance against any forward displacement of said front piston, such that said front piston is prevented from moving forward when there is a vacuum in front of it and essentially atmospheric pressure behind it, and that said front piston during a forward displacement through said constriction while overcoming said resistance is deformed such that said liquid bypass connection is established.

2. An injection cartridge according to claim 1, characterized in that the barrel of the cartridge has an oval cross-section at said constriction.

3. An injection cartridge according to claim 2, characterized in that the rear chamber, containing the liquid component, is closed at its rear end by a displaceable rear piston which on being urged toward exerts a pressure on the front piston to urge it into and through said constriction while overcoming said resistance.

4. An injection cartridge according to claim 2, characterized in that the liquid component in the rear chamber is sterile water or a sterile aqueous solution.

5. An injection cartridge according to claim 1, characterized in that the barrel of the cartridge has a dumbbell-shaped cross-section at said constriction.

6. An injection cartridge according to claim 5, characterized in that the rear chamber, containing the liquid component, is closed at its rear end by a displaceable rear piston which on being urged forward exerts a pressure on the front piston to urge it into and through said constriction while overcoming said resistance.

7. An injection cartridge according to claim 5, characterized in that the liquid component in the rear chamber is sterile water or a sterile aqueous solution.

8. An injection cartridge according to claim 1, characterized in that the rear chamber, containing the liquid component, is closed at its rear end by a displaceable rear piston which on being urged forward exerts a pressure on the front piston to urge it into and through said constriction while overcoming said resistance.

9. An injection cartridge according to claim 8, characterized in that the liquid component in the rear chamber is sterile water or a sterile aqueous solution.

10. An injection cartridge according to claim 1, characterized in that the liquid component in the rear chamber is sterile water or a sterile aqueous solution.

* * * * *